United States Patent
Gryczke

(10) Patent No.: US 8,216,613 B2
(45) Date of Patent: Jul. 10, 2012

(54) PELLETS HAVING A GASTRIC JUICE-RESISTANT ACTIVE COMPOUND MATRIX

(75) Inventor: Andreas Gryczke, Riedstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 834 days.

(21) Appl. No.: 12/034,943

(22) Filed: Feb. 21, 2008

(65) Prior Publication Data

US 2008/0206350 A1     Aug. 28, 2008

Related U.S. Application Data

(60) Provisional application No. 60/908,858, filed on Mar. 29, 2007.

(30) Foreign Application Priority Data

Feb. 22, 2007   (DE) .......................... 10 2007 009 242

(51) Int. Cl.
- *A61K 9/16* (2006.01)
- *A61K 47/32* (2006.01)
- *A61K 47/38* (2006.01)

(52) U.S. Cl. ..................... 424/501; 424/500; 514/772.1; 514/781

(58) Field of Classification Search .................. None
See application file for complete search history.

(56) References Cited

U.S. PATENT DOCUMENTS

| | | | |
|---|---|---|---|
| 6,319,520 B1 * | 11/2001 | Wuthrich et al. | ............. 424/482 |
| 2005/0191352 A1 | 9/2005 | Hayes et al. | |

FOREIGN PATENT DOCUMENTS

| | | |
|---|---|---|
| EP | 0334167 | 9/1989 |
| EP | 0 377 517 A2 | 7/1990 |
| EP | 1 618 873 A1 | 1/2006 |
| WO | WO 96/14058 | 5/1996 |
| WO | WO 00/35450 | 6/2000 |
| WO | WO 01/68058 A1 | 9/2001 |
| WO | WO 0235991 A2 * | 5/2002 |
| WO | WO 03/072083 A2 | 9/2003 |
| WO | WO 2004/096185 A1 | 11/2004 |

OTHER PUBLICATIONS

U.S. Appl. No. 12/030,377, filed Feb. 13, 2008, Gryczke, et al.
U.S. Appl. No. 60/908,858, filed Mar. 29, 2007, Gryczke.

* cited by examiner

*Primary Examiner* — Brian-Yong S Kwon
*Assistant Examiner* — Christopher R Lea
(74) *Attorney, Agent, or Firm* — Oblon, Spivak, McClelland, Maier & Neustadt, L.L.P.

(57) ABSTRACT

A pellet or pellets having an average particle size in the range from 300 to 1,100 μm, comprising a pharmaceutically active substance embedded in a polymer matrix of one or more water-insoluble polymers, wherein the polymer matrix additionally contains 10 to 90% by weight of an anionic polymer and with the proviso that the pellets release no more than 10% of the active compound contained in the release test according to USP in artificial gastric juice at pH 1.2 after 120 min and release at least 50% of the active compound contained after altogether a further 300 min at pH 6.8 and/or pH 7.5.

30 Claims, No Drawings

PELLETS HAVING A GASTRIC JUICE-RESISTANT ACTIVE COMPOUND MATRIX

BACKGROUND OF THE INVENTION

1. Field of the Invention

The present invention relates to pellets having a gastric juice-resistant active compound matrix.

2. Discussion of the Background

WO 01/68058 describes pharmaceutical forms formulated to be gastric juice-resistant. The pharmaceutical forms are essentially constructed from a core containing a pharmaceutical active compound, an inner coating of a copolymer or a mixture of copolymers which comprises 85 to 98% by weight of free radical-polymerized $C_1$- to $C_4$-alkyl esters of acrylic or of methacrylic acid and 15 to 2% by weight of (meth)acrylate monomers having a quaternary ammonium group in the alkyl radical and an outer coating of a copolymer which comprises 75 to 95% by weight of free-radical polymerized $C_1$- to $C_4$-alkyl esters of acrylic or of methacrylic acid and 5 to 25% by weight of (meth)acrylate monomers having an anionic group in the alkyl radical.

US 2005/0191352 describes the production of extrudates containing pharmaceutical active compounds having controlled release of active compound by means of melt extrusion. In addition to the active compound, the mixtures to be extruded can contain polymers such as, for example, Eudragit® RS, Eudragit® NE or mixtures of these polymers. The extrusion preferably takes place in a twin-screw extruder. The extrudates discharged can be comminuted and shaped in the hot state by means of rotating knives to give cylindrical or alternatively to give spherical, ellipsoidal or lenticular particles. The active compound-containing particles thus obtained can be further processed, e.g. by filling into capsules, to give multiparticulate pharmaceutical forms.

EP 1 563 897 A1 describes a device for the production of rounded pellets (pelletizer). The device consists of an upstream feed arrangement, for shapable material which is in particular fed from an extruder and a housing having a rotating cutting unit for cutting the material into material sections, and means for generating a stream of gas in the housing, by the action of which the material sections collide with a housing wall, undergoing rounding. Preferably, the housing wall is cooled in order to reduce the material removed. The device is suitable in particular for the production of pellets for the pharmaceutical sector by mixing pharmaceutical excipients, such as, for example, polymers, with at least one pharmaceutical active compound in the extruder, the extrudates emerging through a nozzle in the cutter housing and being comminuted and rounded by die-face cutting with gas cooling to give pellets.

WO 96/14058 describes melt-extruded oral opioid formulations. Mixtures of the active compound oxycodone HCl, Eudragit® RS, Eudragit® L and stearic acid, for example, are proposed. According to Example 13, the corresponding proportions of the four substances can be 25.0/48.75/3.75 and 22.5%. The substances are first mixed, subsequently extruded at about 83° C. in an extruder, fed to a pelletizer, comminuted to give pellets of about 1.5 mm and then filled into capsules. Formulation according to Example 13 already releases 20% of the active compound contained after 2 h in artificial gastric juice and is therefore not gastric juice-resistant. In artificial intestinal juice, the active compound is released continuously with a delay, such that after 8 h at pH 7.5 approximately 44% of the active compound is released.

Pharmaceutical forms having gastric juice-resistant coatings, such as are known, for example, from WO 01/68058 have drawbacks. For example, the pharmaceutical form described in WO 01/68058 is complex in its production due to its layer structure.

SUMMARY OF THE INVENTION

It is therefore an object of the present invention to provide gastric juice-resistant pharmaceutical forms or their precursors which can be prepared more easily and cost-efficient.

This and other objects have been achieved by the present invention the first embodiment of which includes a pellet, comprising:

a pharmaceutically active substance embedded in a polymer matrix of one or more water-insoluble polymers;

wherein said polymer matrix comprises 10 to 90% by weight of an anionic polymer;

with the proviso that the pellet releases no more than 10% of said active compound in a release test according to USP in artificial gastric juice at pH 1.2 after 120 min, and releases at least 50% of the active compound after altogether a further 300 min at pH 6.8 and/or pH 7.5;

wherein said pellet has a particle size in the range from 300 to 1100 µm.

In another embodiment, the present invention relates to a process for the production of pellets as above, comprising:

mixing the pharmaceutically active substance, the water-insoluble polymer(s) and the anionic polymer, to obtain a mixture; and maintaining said mixture for at least 10 sec at a temperature of at least 5° C. above the glass transition temperature of the polymer or, in the case of a polymer mixture, based on the polymer having the highest glass transition temperature;

extruding said mixture in an extruder, to obtain an extruded mixture; and discharging the extruded mixture by die-face cutting with subsequent rounding to give pellets having a weight average particle size in the range from 300 to 1100 µm.

In another embodiment, the present invention relates to a method of delayed release of a pharmaceutically active compound, comprising:

administering a pellet as above to an organism in need thereof.

DETAILED DESCRIPTION OF THE INVENTION

One object is achieved in particular by pellets having a weight average particle size in the range from 300 to 1100 µm, comprising a pharmaceutically active substance embedded in a polymer matrix of one or more water-insoluble polymers, characterized in that the polymer matrix additionally contains 10 to 90% by weight of an anionic polymer and with the proviso that the pellets release no more than 10% of the active compound contained in the release test according to USP in artificial gastric juice at pH 1.2 after 120 min and release at least 50% of the active compound contained after altogether a further 300 min (altogether 420 min) at pH 6.8 and/or at pH 7.5.

Pellets

The invention relates in particular to pellets having a weight average particle size in the range from 300 to 1100 µm, preferably from 400 to 1000 µm, particularly preferably from 500 to 900 µm, comprising a pharmaceutically active substance embedded in a polymer matrix of one or more water-insoluble polymers, characterized in that the polymer matrix additionally contains 10 to 90, preferably 20 to 90, in particular 50 to 90, % by weight of an anionic polymer, based on the weight of the matrix. The weight average particle size includes all values and subvalues therebetween, especially including 400, 500, 600, 700, 800, 900 and 1000 µm. The amount of anionic polymer includes all values and subvalues therebetween, especially including 20, 30, 40, 50, 60, 70 and 80% by weight.

In the context of the present invention, the weight average particle size is determined by sieving different fractions in size, weighing the fractions and calculating the average particle size from the weights. The method is well known to a skilled person in the field of the invention.

The proportion of active compound can be, based on the pellet weight, 0.1 to 70, preferably 1 to 60, in particular 5 to 50, % by weight. The amount of active compound includes all values and subvalues therebetween, especially including 0.5, 1, 5, 10, 20, 30, 40, 50, and 60% by weight.

The proportion of the polymer matrix can be, based on the pellet weight, 20 to 99.9, preferably 30 to 90, in particular 40 to 80, % by weight. The proportion of the matrix includes all values and subvalues therebetween, especially including 30, 40, 50, 60, 70, 80, 90, 95 and 99% by weight.

The pellets can furthermore contain pharmaceutically customary excipients.

Water-Insoluble Polymers

Water-insoluble polymers are understood as meaning those polymers which over the entire pH range from 1 to 14 are water-insoluble or only swellable in water. Usually, only one water-insoluble polymer is contained in the pharmaceutical composition. Optionally, however, two or more water-insoluble polymers can also be present together or in a mixture.

The water-insoluble polymer presumably has the function of stabilizing the poorly water-soluble active compound in the state of higher solubility after release from the matrix over a relatively long period of time and thus of slowing or of preventing aggregation, recrystallization or precipitation which would reduce solubility. Water-insoluble polymers within the meaning of the invention are synonymous with release-delaying polymers.

Examples of suitable water-insoluble polymers are in particular:

Neutral (meth)acrylate copolymers (EUDRAGIT® NE type)

Neutral or essentially neutral methacrylate copolymers can consist in particular of at least 95, in particular at least 98, preferably at least 99, in particular to at least 99, particularly preferably to 100% by weight of free radical-polymerized (meth)acrylate monomers having neutral radicals, in particular $C_1$- to $C_4$-alkyl radicals.

In the context of the present invention, "essentially neutral" shall mean those neutral (meth)acrylate copolymers which may contain up to less than 5% radicals from anionic monomers. Because of the presence of the anionic groups they are not neutral but essentially neutral. Essentially neutral (meth)acrylate copolymers function in the same way as (totally) neutral (meth)acrylate copolymers in that they are water-insoluble and only swellable in water.

Suitable (meth)acrylate monomers having neutral radicals are, for example, methyl methacrylate, ethyl methacrylate, butyl methacrylate, methyl acrylate, ethyl acrylate, butyl acrylate. Methyl methacrylate, ethyl acrylate and methyl acrylate are preferred.

In small proportions, to less than 5, preferably at most 2, particularly preferably at most 1 or 0.05 to 1, % by weight, methacrylate monomers having anionic radicals, e.g. acrylic acid and/or methacrylic acid, can be contained.

Neutral or nearly neutral (meth)acrylate copolymers of 20 to 40% by weight of ethyl acrylate, 60 to 80% by weight of methyl methacrylate and 0 to less than 5, preferably 0 to 2 or 0.05 to 1, % by weight (EUDRAGIT® NE type), for example, are suitable.

EUDRAGIT® NE is a copolymer of 30% by weight of ethyl acrylate and 70% by weight of methyl methacrylate.

Neutral or essentially neutral methyl acrylate copolymers which have been prepared according to WO 01/68767 as dispersions using 1-10% by weight of a non-ionic emulsifier having an HLB of 15.2 to 17.3 are preferred. The latter offer the advantage that phase separation with formation of crystal structures by the emulsifier is suppressed (EUDRAGIT® NM type).

According to EP 1 571 164 A2, appropriate, nearly neutral (meth)acrylate copolymers, containing low proportions, 0.05 to 1% by weight, of monoolefinically unsaturated C3-C8-carboxylic acids, however, can also be prepared by emulsion polymerization in the presence of comparatively small amounts of anionic emulsifiers, e.g. 0.001 to 1% by weight.

(Meth)acrylate Copolymers Having Quaternary Amino Groups (EUDRAGIT® RS/RL Type)

Further suitable, water-insoluble (meth)acrylate copolymers are known, for example, from EP-A 181 515 or from DE-PS 1 617 751. They are, independently of the pH, soluble or swellable polymers which are suitable for pharmaceutical coatings. A possible preparation process which may be mentioned is substance polymerization in the presence of a free radical-forming initiator dissolved in the monomer mixture. Likewise, the polymer can also be prepared by means of solution or precipitation polymerization. The polymer can in this way be obtained in the form of a fine powder, which is achievable in substance polymerization by grinding, in solution and precipitation polymerization, for example, by spray-drying.

The water-insoluble polymer can be a polymer of 98 to 85% by weight of $C_1$- to $C_4$-alkyl esters of acrylic or of methacrylic acid and 2 to 15% by weight of (meth)acrylate monomers having a quaternary ammonium group or a mixture of a number of polymers of this substance class.

The water-insoluble polymer can be a polymer of 97 to more than 93% by weight of $C_1$- to $C_4$-alkyl esters of acrylic or methacrylic acid and 3 to less than 7% by weight of (meth) acrylate monomers having a quaternary ammonium group (Eudragit® RS type).

Preferred $C_1$- to $C_4$-alkyl esters of acrylic or of methacrylic acid are methyl acrylate, ethyl acrylate, butyl acrylate, butyl methacrylate and methyl methacrylate.

As a (meth)acrylate monomer having quaternary amino groups, 2-trimethylammoniumethyl methacrylate chloride is particularly preferred.

A specifically suitable copolymer contains 65% by weight of methyl methacrylate, 30% by weight of ethyl acrylate and 5% by weight of 2-trimethylammoniumethyl methacrylate chloride (EUDRAGIT® RS).

The water-insoluble polymer can be a polymer of 93 to 88% by weight of $C_1$- to $C_4$-alkyl esters of acrylic or of methacrylic acid and 7 to 12% by weight of (meth)acrylate monomers having a quaternary ammonium group (Eudragit(® RL type).

A specifically suitable copolymer contains, for example, 60% by weight of methyl methacrylate, 30% by weight of ethyl acrylate and 10% by weight of 2-trimethylammoniumethyl methacrylate chloride (EUDRAGIT® RL).

The water-insoluble polymer can be a mixture of the polymers of the type Eudragit® RS and of the type Eudragit® RL in the ratio 20:1 to 1:20.

In particular, mixtures of EUDRAGIT® RS and EUDRAGIT® RL, e.g. in the ratio from 20:1 to 1:20 parts by weight, are also suitable.

Polyvinyl acetate/polyvinyl acetate copolymers, ethyl- and methylcellulose

As a water-insoluble polymer, the pharmaceutical composition can also contain a polyvinyl acetate, a polyvinyl acetate copolymer (e.g. Kollicoat® SR 30D or Kollidon® SR type), an ethylcellulose or a methylcellulose.

Anionic Polymers

Anionic polymers are preferably understood as meaning polymers having at least 5%, particularly preferably 5 to 75%, of monomer radicals having anionic groups. Anionic (meth) acrylate copolymers are preferred.

(Meth)acrylate Copolymers Having Anionic Groups (EUDRAGIT® L, L100-55, S and FS Types)

Suitable anionic (meth)acrylate copolymers are, for example, polymers of 25 to 95% by weight of $C_1$- to $C_4$-alkyl esters of acrylic or of methacrylic acid and 5 to 75% by weight of (meth)acrylate monomers having an anionic group. Depending on the content of anionic groups and the character of the further monomers at pHs above pH 5.0, appropriate polymers are water-soluble and thus also intestinal juice-soluble.

Usually, the proportions mentioned add up to 100% by weight. Additionally, however, without this leading to an impairment or change in the essential properties, small amounts in the range from 0 to 10, e.g. 1 to 5, % by weight of further vinylically copolymerizable monomers, such as, for example, hydroxyethyl methacrylate or hydroxyethyl acrylate, can be contained.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group can be, for example, acrylic acid, but preferably methacrylic acid.

Anionic (meth)acrylate copolymers of 40 to 60% by weight of methacrylic acid and 60 to 40% by weight of methyl methacrylate or 60 to 40% by weight of ethyl acrylate (EUDRAGIT® L or EUDRAGIT® L100-55 types) are furthermore suitable.

EUDRAGIT® L is a copolymer of 50% by weight of methyl methacrylate and 50% by weight of methacrylic acid.

EUDRAGIT® L100-55 is a copolymer of 50% by weight of ethyl acrylate and 50% by weight of methacrylic acid. EUDRAGIT® L 30D-55 is a dispersion comprising 30% by weight of EUDRAGIT® L 100-55.

Likewise suitable are anionic (meth)acrylate copolymers of 20 to 40% by weight of methacrylic acid and 80 to 60% by weight of methyl methacrylate (EUDRAGIT® S type).

Furthermore, for example, anionic (meth)acrylate copolymers consisting of 10 to 30% by weight of methyl methacrylate, 50 to 70% by weight of methyl acrylate and 5 to 15% by weight of methacrylic acid (EUDRAGIT® FS type) are suitable.

EUDRAGIT® FS is a copolymer of 25% by weight of methyl methacrylate, 65% by weight of methyl acrylate and 10% by weight of methacrylic acid. EUDRAGIT® FS 30 D is a dispersion comprising 30% by weight of EUDRAGIT® FS.

Furthermore suitable for the purposes of the invention are anionic (meth)acrylate copolymers (see WO 2003/072087) which comprise 20 to 34% by weight of methacrylic acid and/or acrylic acid, 20 to 69% by weight of methyl acrylate and 0 to 40% by weight of ethyl acrylate and/or optionally 0 to 10% by weight of further vinylically copolymerizable monomers, with the proviso that the glass transition temperature of the copolymer according to ISO 11357-2, item 3.3.3, is at most 60° C.

The copolymer can in particular comprise free radical-polymerized units of 20 to 34, preferably 25 to 33, particularly preferably 28 to 32% by weight of methacrylic acid or acrylic acid, preferably methacrylic acid, 20 to 69, preferably 35 to 65, particularly preferably 35 to 55% by weight of methyl acrylate and optionally 0 to 40, preferably 5 to 35, particularly preferably 15 to 35% by weight of ethyl acrylate, with the proviso that the glass transition temperature of the copolymer (measurement without plasticizer addition at a residual monomer content (REMO) of less than 100 ppm, heating rate 10° C./min, nitrogen atmosphere) according to ISO 11357-2, item 3.3.3 ($T_{mg}$), is at most 60, preferably 40 to 60, particularly preferably 45 to 55° C.

The copolymers preferably consist exclusively of the monomers methacrylic acid, methyl acrylate and ethyl acrylate in the proportions indicated above.

Additionally, however, without this leading to an impairment of the essential properties, small amounts in the range from 0 to 10, e.g. 1 to 5, % by weight, of further vinylically copolymerizable monomers, such as, for example, methyl methacrylate, butyl methacrylate, butyl acrylate or hydroxyethyl methacrylate, can be contained.

Glass transition temperature is understood here in particular as meaning the midpoint temperature $T_{mg}$ according to ISO 11357-2, item 3.3.3. Measurement is carried out without plasticizer addition, at residual monomer contents (REMO) of less than 100 ppm, at a heating rate of 10° C./min and under a nitrogen atmosphere.

The copolymers are obtained in a manner known per se by free radical substance, solution, bead or emulsion polymerization. Before processing, they must be brought to the particle size range according to the invention by means of suitable grinding, drying or spraying processes.

This can be carried out by simple breaking of extruded and cooled granule strands or die-face cutting.

In particular when mixing with further powders or liquids, the use of powders can be advantageous. Suitable implements for the production of the powders are familiar to the person skilled in the art, e.g. air jet mills, pinned disc mills, fan mills. Optionally, appropriate screening steps can be included. A suitable mill for large industrial amounts is, for example, a counter jet mill (Multi No. 4200), which is operated at about 6 bar overpressure.

Furthermore suitable for the purposes of the invention are anionic (meth)acrylate copolymers (see WO 2004/096185) comprising 20 to 33% by weight of methacrylic acid and/or acrylic acid, 5 to 30% by weight of methyl acrylate and 20 to 40% by weight of ethyl acrylate and greater than 10 to 30% by weight of butyl methacrylate and optionally 0 to 10% by weight of further vinylically copolymerizable monomers, where the proportions of the monomers add up to 100% by weight, with the proviso that the glass transition temperature of the copolymers according to ISO 11357-2, item 3.3.3 (midpoint temperature $T_{mg}$), is 55 to 70° C.

The abovementioned copolymers in particular comprise free radical-polymerized units of 20 to 33, preferably 25 to 32, particularly preferably 28 to 31, % by weight of methacrylic acid or acrylic acid; methacrylic acid is preferred, 5 to 30, preferably 10 to 28, particularly preferably 15 to 25, % by weight of methyl acrylate, 20 to 40, preferably 25 to 35, particularly preferably 28 to 32, % by weight of ethyl acrylate, and greater than 10 to 30, preferably 15 to 25, particularly preferably 18 to 22, % by weight of butyl methacrylate, where the monomer composition is chosen such that the glass transition temperature of the copolymers is 55 to 70° C., preferably 59 to 66, particularly preferably 60 to 65° C.

For the adjustment of special release profiles and/or sites of release, mixtures of the copolymers mentioned can also be used.

Glass transition temperature is understood here in particular as meaning the midpoint temperature $T_{mg}$ according to ISO 11357-2, item 3.3.3. Measurement is carried out without plasticizer addition, at residual monomer contents (REMO) of less than 100 ppm, at a heating rate of 10° C./min and under a nitrogen atmosphere.

The copolymer preferably consists essentially to exclusively, to 90, 95 or 99 to 100% by weight, of the monomers methacrylic acid, methyl acrylate, ethyl acrylate and butyl methacrylate in the ranges of amounts indicated above.

Additionally, however, without this having to lead to an impairment of the essential properties, small amounts in the range from 0 to 10, e.g. 1 to 5, % by weight, of further vinylically copolymerizable monomers, such as, for example, methyl methacrylate, butyl acrylate, hydroxyethyl methacrylate, vinylpyrrolidone, vinylmalonic acid, styrene, vinyl alcohol, vinyl acetate and/or their derivatives can be contained.

The abovementioned anionic (meth)acrylate copolymers are preferentially obtained in a manner known per se by free radical substance, solution, bead or emulsion polymerization. Before processing, they must be brought to the particle size range according to the invention by means of suitable grinding, drying or spraying processes. This can be carried out by simple breaking of extruded and cooled granule strands or die-face cutting.

The preparation of anionic (meth)acrylate copolymers containing proportions of anionic monomers of over 5% by weight in the polymer can be carried out in a manner known per se by free radical polymerization of the monomers (see, for example, EP 0 704 207 A2, EP 0 704 208 A2, WO 2003/072087, WO 2004/096185). The copolymers can be prepared in a manner known per se by free radical emulsion polymerization in the aqueous phase in the presence of preferably anionic emulsifiers, for example according to the process described in DE-C 2 135 073.

In particular when mixing with further powders or liquids, the use of powders can be advantageous. Suitable implements for the preparation of the powders are familiar to the person skilled in the art, e.g. air jet mills, pinned disc mills, fan mills. Optionally, appropriate screening steps can be included. A suitable mill for large industrial amounts is, for example, a counter jet mill (Multi No. 4200), which is operated at about 6 bar overpressure.

The copolymers can be prepared continuously or batchwise (batch process) in substance, in solution, by bead polymerization or in emulsion according to customary processes of free radical polymerization in the presence of free radical-forming initiators and optionally regulators for the adjustment of the molecular weight. The average molecular weight Mw (weight average, determined, for example, by measurement of the solution viscosity) can be, for example, in the range from 80 000 to 1 000 000 (g/mol). Preferably, the emulsion polymerization is carried out in the aqueous phase in the presence of water-dissolved initiators and (preferably anionic) emulsifiers. In the case of substance polymerization, the copolymer can be obtained in solid form by breaking, extrusion, granulation or die-face cutting.

Pharmaceutically Active Substance

The pharmaceutically active substance contained in the pellets can be a pharmaceutical active compound or a food supplement in the widest sense.

Preferably, one or more of the following pharmaceutically active substances is contained: acamprosate, aceclofenac, acemetacin, acetylcysteine, acetylsalicylic acid, acetyltyrosine, acipimox, acitretin, alanine, alendronic acid, amethopterin, amino acids, amoxicillin, ampicillin, ascorbic acid, atorvastatin, azidocillin, aztreonam, bacampicillin, baclofen, benazepril, bendamustine, benzylpenicillin, bezafibrate, biotin, bornaprine, bumetanide, cabastine, canrenoic acid, carbamoylphenoxyacetic acid, carbidopa, carbimazole, carbocisteine, carisoprodol, cefaclor, cefadroxil, cefalexin, cefazoline, cefepime, cefetamet, cefixime, cefotaxime, cefotiam, cefoxitine, cefpodoxime, ceftazidime, ceftibutene, ceftriaxone, cefuroxime, cetirizine, chenodeoxycholic acid, chlorambucil, cidofovir, cilastatin, cilazapril, cinoxacine, ciprofloxacin, cisatracurium besilate, clavulanic acid, clodronic acid, clorazepate, cromoglicic acid, desmeninol, diclofenac, dicloxacillin, enoxacin, eprosartan, ethacrynic acid, etidronic acid, etofylline, etomidate, felbinac, felodipine, fenofibrate, fexofenadine, flavoxate, fleroxacine, flucloxacillin, flufenaminic acid, flumazenil, flupirtine, flurbiprofen, fluvastatin, fosfomycin, fosinopril, furosemide, fusidic acid, gabapentin, gemfibrozil, ibandronic acid, ibuprofen, iloprost, imidapril, imipenem, indomethacin, irinotecan, isradipine, ketoprofen, lercanidipine, levodopa, levofloxacin, liothyronine, lipoic acid, lisinopril, lodoxamide, lomefloxacin, lonazolac, loracarbef, loratadine, lovastatin, mefenamic acid, meropenem, mesalazine, metamizole, methotrexate, methyldopa, mezlocillin, moexipril, montelukast, moxifloxacin, mupirocin, naproxen, natamycin, nateglinide, nedocromil, nicotinic acid, nifedipine, nilvadipine, nimodipine, nisoldipine, nitrendipine, norfloxacin, ofloxacin, olsalazine, orotic acid, oxacillin, pamidronic acid, pangamic acid, penicillamine, phenoxymethylpenicillin, pentosan polysulphate, perindopril, pethidine, pipemidic acid, piperacillin, pirenoxine, piretanide, probenecid, proglumide, propicillin, prostaglandins, quinapril, quinaprilate, ramipril, repaglinide, reserpine, risedronic acid, salicylic acid, spirapril, sulbactam, sulphasalazine, sultamicillin, tazarotene, tazobactam, telmisartan, tiagabine, tiaprofenic acid, tilidine, tiludronic acid, trandolapril, tranexamic acid, valproic acid, vigabatrine, vincamine, vinpocetine, zanamivir, zoledronic acid, zopiclone, and their salts, isomers and combinations.

Release-Delaying Coatings

The pellets can additionally be provided with a coating of a release-delaying polymer. The comparatively high density of the pellets and their extremely low friability makes it possible to apply very thin polymer coatings. The release-delaying polymer coating can therefore preferably be, for example, only 1 to 10, preferably 2-7, % by weight based on the pellet weight.

Delayed Release Pharmaceutical Forms

Delayed release pharmaceutical forms or pharmaceutical forms coated with release-delaying coatings are generally understood as meaning pharmaceutical forms having sustained release of active compound (sustained-release type), prolonged release of active compound (prolonged-release type), graded release of active compound (repeat action- or layered-time-action type) or delayed release of active compound (delayed-release type), which are intended for oral ingestion. The release of active compound should usually be controlled over a relatively long period of time, so long-lasting blood level concentrations of the active compound in the therapeutically optimal range are brought about.

Multiparticulate Pharmaceutical Forms

The pellets according to the invention are in particular suitable as precursors for the production of multiparticulate pharmaceutical forms. The pellets can accordingly be used for the production of multiparticulate pharmaceutical forms.

The pellets can thus be contained in multiparticulate pharmaceutical forms of all types, in particular in pellet-containing tablets, minitablets, capsules, sachets or inspissated juices.

The production of multiparticulate pharmaceutical forms by compression of a pharmaceutically customary binder with active compound-containing particles is described in detail, for example, in Beckert et al. (1996), "Compression of enteric-coated pellets to disintegrating tablets", *International Journal of Pharmaceutics* 143, pp. 13-23, and in WO 96/01624.

Mixtures for the production of tablets from coated particles can be prepared by mixing the pellets with suitable binders for tabletting, if necessary the addition of disintegration-promoting substances and if necessary the addition of lubricants. Mixing can be carried out in suitable machines. By premixing the pellets with the lubricants or mould release agent magnesium stearate, their surface can be hydrophobized and thus sticking can be avoided.

Mixtures suitable for tabletting can customarily contain 3 to 15% by weight of a disintegrant, e.g. Kollidon C L and, for example, 0.1 to 1% by weight of a lubricant and mould release agent such as magnesium stearate. The proportion of binder is determined according to the proportion of coated particles required.

Typical binders for multiparticulate pharmaceutical forms are, for example, Cellactose®, microcrystalline cellulose, calcium phosphates, Ludipress(®, lactose or other suitable sugars, calcium sulphates or starch derivatives. Preferably, substances having a low bulk density are employed.

Typical disintegrants are crosslinked starch or cellulose derivatives, and crosslinked polyvinylpyrrolidone. Cellulose derivatives are also suitable. The use of disintegrants can be dispensed with by means of choice of a suitable binder.

Typical lubricants and mould release agents are magnesium stearates or other suitable salts of fatty acids or substances mentioned in the literature for this purpose (e.g. lauric acid, calcium stearate, talc etc.). When using suitable machines (e.g. a tablet press with external lubrication) or suitable formulations, the use of a lubricant and mould release agent in the mixture can be dispensed with.

Excipients for flow improvement (e.g. highly disperse silicic acid derivatives, talc etc.) can optionally be added to the mixtures.

Tabletting can take place in customary tablet presses, eccentric or rotary tablet presses, at compressive forces in the range from 5 to 40 kN, preferably 10-20 kN. The tablet presses can be equipped with systems for external lubrication. Optionally, special systems for matrix filling are used, which avoid matrix filling by means of stirrer blades.

Process for the Production of the Pellets According to the Invention

The invention furthermore relates to a process for the production of pellets according to the invention, where the pharmaceutically active substance, the water-insoluble polymer(s) and the anionic polymer are mixed and a temperature of at least 5, preferably of at least 10° C. above the glass transition temperature of the polymer having the highest glass transition temperature acts for at least 10, preferably for at least 20, sec, the mixture is extruded in an extruder, preferably a twin-screw extruder, and is discharged by die-face cutting with subsequent rounding to give pellets having a weight average particle size in the range from 300 to 1100 μm.

Preferably, for the die-face cutting and the rounding to give pellets a device for the production of rounded pellets (pelletizer) is employed, as is known to the person skilled in the art, for example, from EP 1 563 897 A1. A suitable device consists, for example, of an upstream feed device for the material fed from the extruder, and a housing having a rotating cutting unit for cutting the material into material sections, and means for the production of a gas stream in the housing, by means of which the material selections collide with a housing wall, where they undergo rounding. Preferably, the housing wall is cooled in order to reduce the material removed.

Pharmaceutically customary excipients can be added to the polymer matrix in the production of the pellets.

A temperature of at least 5, preferably of at least 10° C. above the glass transition temperature of the polymer having the highest glass transition temperature should act on the mixture to be processed for at least 10, preferably for at least 20, sec as a minimum requirement. This causes the formation of a uniform melt phase. Often, but not always, the anionic polymer has a higher glass transition temperature than water-insoluble polymer, so the anionic polymer is to be used as a reference point for the minimum requirement on the processing temperature.

Glass transition temperature is understood here in particular as meaning the midpoint temperature $T_{mg}$ according to ISO 11357-2, item 3.3.3. The measurement is carried out without plasticizer addition, at residual monomer contents (REMO) of less than 100 ppm, at a heating rate of 10° C./min and under a nitrogen atmosphere.

A mixture for the production of pellets according to the invention can be comprise, for example, 20% by weight of a pharmaceutically active substance, embedded in a matrix of 75% by weight of the water-insoluble polymer Eudragit® RS and 5% by weight of the anionic polymer Eudragit® L. The glass transition temperature of Eudragit® RS is approximately 50° C., that of Eudragit® L approximately 150° C. In this case, a temperature of at least 155° C. should act on the mixture for at least 5 sec.

A mixture for the production of pellets according to the invention can comprise, for example, 20% by weight of a pharmaceutically active substance embedded in a matrix of 75% by weight of the water-insoluble polymer Eudragit® RS and 5% by weight of the anionic polymer Eudragit® FS. The glass transition temperature of Eudragit® RS is approximately 50° C., that of Eudragit® FS approximately 48° C. In this case, a temperature of at least 55° C. should act on the mixture for at least 5 sec.

Under practical conditions, in many cases appropriate minimum temperatures are usually easily achieved or exceeded and also held over relatively long periods of time without this being critical for the pharmaceutically active substance or the polymers contained. Depending on the polymer composition of the mixture, typical processing temperatures in the extruder can be, for example, 50 to 200, preferably 100 to 180° C.

Depending on the mixture constituents, in particular the pharmaceutically active substances contained, care is to be taken, however, that temperatures and residence times are calculated such that heat damage or adverse effects are avoided if possible. Usually, it will be attempted to set the processing temperatures and the residence times as low as possible first. With knowledge of the invention, a person skilled in the art can apply this easily to the individual case and proceed appropriately.

Release of Active Compound According to USP (United States Pharmacopeia)

The release of active compound can be determined according to USP, in particular USP 28-NF23, General Chapter <711>, *Dissolution*, Apparatus 2 (Paddle), method <724> "Delayed Release (Enteric Coated) Articles-General General Drug Release Standard", Method B (100 rpm, 37° C.) with the following modification: The pellets were first tested for gastric juice resistance for 120 min in artificial gastric juice (USP) at pH 1.2, subsequently the mixture is rebuffered to pH 6.8 or 7.5 using phosphate buffer, which corresponds to an artificial intestinal medium. The active compound concentration in the test medium can be determined depending on the active compound, e.g. photometrically.

The present invention also relates to a method of delayed release of a pharmaceutically active compound, comprising: administering a pellet according to the invention to an organism in need thereof. An organism in need of the pharmaceutically active compound includes humans and mammals.

Having generally described this invention, a further understanding can be obtained by reference to certain specific examples which are provided herein for purposes of illustration only, and are not intended to be limiting unless otherwise specified.

EXAMPLES

All examples were extruded in a synchronous 18 mm twin-screw extruder having a functional length of the process part of 40D. The extrusion temperature in the entry area was 10° C.-100° C., in the following cylinders of the extruder the temperature was increased to 160° C. The melt was discharged at 160° C. and cut to give pellets in an air-cooled die-face cutting process. For the die-face cutting process, the melt was led at the end of the extrusion process part into a conical melt channel, which at the end had a number of outlet openings at the base in the form of a ring. Above this ring rotated one or more knives, which cut off the melt in the hot state. The pellets were cooled in a stream of air and transported away. The rounding of the pellets was carried out by means of the surface tension still present in the melt and not or only to a very small extent during the transport of the pellets directly after the cutting process. The active compound and the polymers were fed to the extruder by means of gravimetric metering.

Examples C1 to C9, C11 to C15 and C19 were comparative examples:

The pellets of Example C1 contained the water-insoluble polymer Eudragit® RS and no water-soluble polymer. The formulation shows a delayed release of active compound, but was not gastric juice-resistant, as after 120 min at pH 1.2 already 19.8% of the active compound initially contained was released.

The pellets of Examples C2, C3, C4 and C6 contained the water-insoluble polymer Eudragit® RS and a water-soluble polymer not according to the invention, Eudragit® E PO. The pellets in Example C5 contained no water-insoluble polymer, but only the water-soluble polymer not according to the invention, Eudragit® E PO. In all cases, the active compound was already released to more than 40% after 30 min at pH 1.2, so no gastric juice resistance whatsoever exists.

Examples C7 to C9 contained the water-insoluble polymer Eudragit® RL and the anionic polymer according to the invention, Eudragit® FS, but not in an adequate amount, at most 30% by weight in C9, and do not have adequate gastric juice resistance, as after 120 min at pH 1.2 they clearly release more than 10% of the active compound initially contained. The pellets of Example C11, for comparison, only contained the anionic polymer Eudragit® FS. The formulation shows a delayed release of active compound, but was not gastric juice-resistant, as after 120 min at pH 1.2 already 14.4% of the active compound initially contained was released.

Examples C12 to C15 contained the water-insoluble polymer Eudragit® RS and the anionic polymer according to the invention Eudragit® FS in different admixtures. Even from a proportion of 4% by weight of Eudragit® FS based on the polymer mixture in Example C12, with only 9.1% release of active compound gastric juice resistance, a degree of release of less than 10%, was achieved. However, the release of the formulations was so strongly delayed that even after 420 min at most 20.3% (C13) of the active compound contained was released. This was too low, the greater proportion of the active compound would have been excreted again without having been absorbed by the body.

Examples 10, 16-18, 20 were examples according to the invention:

Example 10 contained the water-insoluble polymer Eudragit® RL and the water-soluble polymer according to the invention Eudragit® FS in a proportion of 40% by weight, or 80% by weight in the polymer mixture. The formulation was gastric juice-resistant, as after 120 min at pH 1.2 only 9.1% of the active compound initially contained was released. At pH 6.8 up to the time 240 min, virtually no further release of active compound (11.1%) takes place. After rebuffering to pH 7.5 the active compound was released rapidly to 100% up to the time 360 min.

Examples 16 to 18 contained the water-insoluble polymer Eudragit® RS and the water-soluble polymer according to the invention Eudragit® FS in different admixtures. From a proportion of 20% by weight of Eudragit® FS in the formulation or 40% by weight based on the polymer mixture in Example 16, after rebuffering to pH 7.5 the commencement of markedly accelerated release of active compound was seen.

Example 20 contained the water-insoluble polymer Eudragit® NE and the water-soluble polymer according to the invention Eudragit® FS. The formulation was gastric juice-resistant, as after 120 min at pH 1.2 only 8.1% of the active compound initially contained was released. After rebuffering to pH 6.8, the active compound was rapidly released to 100% up to the time 300 min.

Examples

Comparative Examples C1 to C6

|  |  | Example No. | | | | | |
| --- | --- | --- | --- | --- | --- | --- | --- |
|  |  | C1 | C2 | C3 | C4 | C5 | C6 |
|  |  | Theophylline [% by weight] | | | | | |
|  |  | 50 | 50 | 50 | 50 | 50 | 50 |
|  |  | Eudragit ® E PO [% by weight] | | | | | |
|  |  | 0 | 10 | 20 | 40 | 50 | 30 |
|  |  | Eudragit ® RS [% by weight] | | | | | |
|  |  | 50 | 40 | 30 | 10 | 0 | 20 |
| pH of the medium | Time [min] | Release of active compound [%] | | | | | |
| 1.2 | 0 | 0.0 | 0.0 | 0.0 | 0.0 | 0.0 | 0.0 |
| 1.2 | 5 | 3.1 | 48.0 | 67.9 | 83.4 | 106.2 | 78.4 |
| 1.2 | 10 | 5.1 | 67.4 | 87.1 | 99.9 | 105.8 | 94.7 |
| 1.2 | 15 | 6.3 | 78.7 | 96.5 | 103.5 | 105.9 | 101.4 |
| 1.2 | 30 | 9.1 | 86.2 | 100.5 | 103.4 | 106.0 | 102.9 |

Comparative Examples C7, C8, C9 and C11 and Example 10 According to the Invention

| | | | Example No. | | | |
|---|---|---|---|---|---|---|
| | | C7 | C8 | C9 | 10 | C11 |
| | | \multicolumn{5}{c}{Theophylline [% by weight]} | | | | |
| | | 50 | 50 | 50 | 50 | 50 |
| | | \multicolumn{5}{c}{Eudragit ® RL [% by weight]} | | | | |
| | | 40 | 30 | 20 | 10 | 0 |
| | | \multicolumn{5}{c}{Eudragit ® FS [% by weight]} | | | | |
| pH of the medium | Time [min] | 10 | 20 | 30 | 40 | 50 |
| | | \multicolumn{5}{c}{Release of active compound [%]} | | | | |
| 1.2 | 0   | 0.0  | 0.0  | 0.0  | 0.0  | 0.0 |
| 1.2 | 30  | 36.0 | 16.4 | 6.9  | 5.3  | 9.4 |
| 1.2 | 60  | 55.9 | 29.8 | 11.9 | 6.8  | 11.6 |
| 1.2 | 90  | 70.2 | 41.9 | 19.0 | 8.0  | 13.2 |
| 1.2 | 120 | 80.7 | 52.5 | 27.1 | 9.1  | 14.4 |
| 1.2 | 135 | 82.3 | 53.9 | 27.9 | 9.3  | 15.9 |
| 6.8 | 140 | 82.8 | 54.1 | 28.1 | 9.4  | 16.3 |
| 6.8 | 150 | 83.6 | 54.5 | 28.3 | 9.6  | 17.2 |
| 6.8 | 165 | 84.5 | 55.0 | 28.6 | 9.9  | 18.3 |
| 6.8 | 180 | 85.3 | 55.4 | 28.9 | 10.2 | 19.5 |
| 6.8 | 210 | 86.4 | 56.1 | 29.3 | 10.9 | 21.6 |
| 6.8 | 240 | 87.2 | 56.7 | 29.7 | 11.6 | 23.8 |
| 7.5 | 250 | 90.3 | 58.8 | 33.8 | 31.1 | 42.7 |
| 7.5 | 260 | 90.4 | 59.5 | 40.7 | 45.6 | 56.4 |
| 7.5 | 270 | 90.7 | 60.1 | 48.2 | 55.9 | 66.1 |
| 7.5 | 285 | 90.9 | 61.1 | 57.9 | 67.5 | 77.0 |
| 7.5 | 300 | 91.2 | 62.1 | 65.5 | 76.3 | 84.8 |
| 7.5 | 330 | 91.6 | 64.1 | 77.0 | 88.6 | 95.1 |
| 7.5 | 360 | 92.0 | 66.5 | 85.1 | 96.3 | 100.6 |

EUDRAGIT ® RL: copolymer of 6% by weight of methyl methacrylate, 30% by weight of ethyl acrylate and 10% by weight of 2-trimethylammoniumethyl methacrylate chloride.
EUDRAGIT ® FS: copolymer of 65% by weight of methyl acrylate, 25% by weight of methyl methacrylate and 10% by weight of methacrylic acid

-continued

| | | Example No. | | | | | |
|---|---|---|---|---|---|---|---|
| | | C1 | C2 | C3 | C4 | C5 | C6 |
| | | \multicolumn{6}{c}{Theophylline [% by weight]} | | | | | |
| | | 50 | 50 | 50 | 50 | 50 | 50 |
| | | \multicolumn{6}{c}{Eudragit ® E PO [% by weight]} | | | | | |
| | | 0 | 10 | 20 | 40 | 50 | 30 |
| | | \multicolumn{6}{c}{Eudragit ® RS [% by weight]} | | | | | |
| pH of the medium | Time [min] | 50 | 40 | 30 | 10 | 0 | 20 |
| | | \multicolumn{6}{c}{Release of active compound [%]} | | | | | |
| 1.2 | 45  | 11.3 | 87.8 | 100.7 | 102.8 | 105.1 | 102.1 |
| 1.2 | 60  | 13.3 | 88.5 | 100.9 | 102.9 | 105.1 | 102.1 |
| 1.2 | 90  | 16.8 | 89.5 | 101.2 | 102.8 | 105.3 | 102.2 |
| 1.2 | 120 | 19.8 | 90.9 | 101.5 | 102.9 | 105.1 | 102.1 |
| 6.8 | 140 | 21.6 | 92.1 | 101.7 | 103.0 | 105.1 | 102.1 |
| 6.8 | 150 | 21.9 | 94.1 | 101.9 | 102.9 | 105.3 | 102.2 |
| 6.8 | 165 | 22.9 | 95.7 | 102.0 | 103.0 | 105.3 | 102.3 |
| 6.8 | 180 | 23.8 | 96.9 | 102.0 | 103.1 | 105.3 | 102.3 |
| 6.8 | 210 | 25.5 | 94.1 | 101.9 | 102.9 | 105.3 | 102.2 |
| 6.8 | 240 | 27.1 | 95.7 | 102.0 | 103.0 | 105.3 | 102.3 |
| 6.8 | 300 | 30.1 | 96.9 | 102.0 | 103.1 | 105.3 | 102.3 |
| 6.8 | 360 | 32.8 | 97.8 | 102.1 | 103.1 | 105.4 | 102.4 |
| 6.8 | 420 | 35.2 | 98.6 | 102.2 | 103.0 | 105.5 | 102.4 |

EUDRAGIT ® E PO: copolymer of 25% by weight of methyl methacrylate, 25% by weight of butyl methacrylate and 50% by weight of dimethylaminoethyl methacrylate in powder form
EUDRAGIT ® RS: copolymer of 65% by weight of methyl methacrylate, 30% by weight of ethyl acrylate and 5% by weight of 2-trimethylammoniumethyl methacrylate chloride.

Examples 16 to 18 and 20 According to the Invention and Comparative Examples C12 to C15 and C19

| | | Example No. | | | | | | | | |
|---|---|---|---|---|---|---|---|---|---|---|
| | | C12 | C13 | C14 | C15 | 16 | 17 | 18 | C19 | 20 |
| | | \multicolumn{9}{c}{Theophylline [% by weight]} | | | | | | | | |
| | | 50 | 50 | 50 | 50 | 50 | 50 | 50 | 50 | 50 |
| | | \multicolumn{9}{c}{Eudragit ® RS [% by weight]} | | | | | | | | |
| | | 48 | 46 | 44 | 42 | 30 | 20 | 10 | 0 | 0 |
| | | \multicolumn{9}{c}{Eudragit ® NE} | | | | | | | | |
| | | 0 | 0 | 0 | 0 | 0 | 0 | 0 | 0 | 40 |
| | | \multicolumn{9}{c}{Eudragit ® FS [% by weight]} | | | | | | | | |
| pH of the medium | Time [min] | 2 | 4 | 6 | 8 | 20 | 30 | 40 | 50 | 10 |
| | | \multicolumn{9}{c}{Release of active compound [%]} | | | | | | | | |
| 1.2 | 0   | 0.0  | 0.0  | 0.0  | 0.0  | 0.0  | 0.0  | 0.0  | 0.0  | 0.0 |
| 1.2 | 30  | 5.3  | 6.3  | 5.5  | 3.8  | 3.8  | 4.8  | 5.1  | 9.4  | 5.3 |
| 1.2 | 45  | 6.2  | 7.4  | 6.3  | 4.3  | 4.3  | 5.5  | 5.9  | —    | — |
| 1.2 | 60  | 6.9  | 8.3  | 6.9  | 4.8  | 4.7  | 6.0  | 6.6  | 11.6 | — |
| 1.2 | 90  | 8.2  | 9.8  | 8.0  | 5.6  | 5.5  | 7.0  | 7.7  | 13.2 | 7.4 |
| 1.2 | 120 | 9.3  | 11.2 | 9.0  | 6.3  | 6.2  | 7.8  | 8.7  | 14.4 | 8.1 |
| 6.8 | 140 | 9.7  | 11.8 | 9.4  | 6.4  | 6.4  | 8.1  | 9.5  | 15.9 | 21.0 |
| 6.8 | 150 | 10.0 | 12.1 | 9.6  | 6.6  | 6.5  | 8.3  | 9.7  | 17.2 | 26.1 |
| 6.8 | 165 | 10.3 | 12.6 | 9.9  | 6.8  | 6.7  | 8.5  | 10.0 | 18.3 | 32.6 |
| 6.8 | 180 | 10.7 | 13.0 | 10.2 | 7.0  | 6.9  | 8.7  | 10.3 | 19.5 | 38.3 |
| 7.5 | 195 | 11.2 | 13.9 | 10.8 | 7.0  | 9.9  | 30.5 | 41.5 | 42.7 | 45.1 |
| 7.5 | 210 | 11.6 | 14.4 | 11.1 | 7.2  | 14.3 | 45.0 | 59.8 | 66.1 | 58.9 |

-continued

| | | Example No. | | | | | | | | |
|---|---|---|---|---|---|---|---|---|---|---|
| | | C12 | C13 | C14 | C15 | 16 | 17 | 18 | C19 | 20 |
| | | Theophylline [% by weight] | | | | | | | | |
| | | 50 | 50 | 50 | 50 | 50 | 50 | 50 | 50 | 50 |
| | | Eudragit ® RS [% by weight] | | | | | | | | |
| | | 48 | 46 | 44 | 42 | 30 | 20 | 10 | 0 | 0 |
| | | Eudragit ® NE | | | | | | | | |
| | | 0 | 0 | 0 | 0 | 0 | 0 | 0 | 0 | 40 |
| | | Eudragit ® FS [% by weight] | | | | | | | | |
| pH of the medium | Time [min] | 2 | 4 | 6 | 8 | 20 | 30 | 40 | 50 | 10 |
| | | Release of active compound [%] | | | | | | | | |
| 7.5 | 225 | 11.9 | 14.9 | 11.4 | 7.4 | 18.2 | 55.7 | 72.6 | 77.0 | 67.9 |
| 7.5 | 240 | 12.3 | 15.3 | 11.7 | 7.6 | 21.8 | 64.3 | 82.2 | 84.8 | 75.9 |
| 7.5 | 270 | 12.9 | 16.2 | 12.3 | 8.1 | 28.3 | 77.6 | 95.4 | 95.1 | 91.4 |
| 7.5 | 300 | 13.6 | 17.1 | 12.9 | 8.5 | 34.1 | 87.3 | 102.3 | 100.6 | 100.9 |
| 7.5 | 330 | 14.2 | 17.9 | 13.4 | 8.9 | 39.4 | 94.5 | 104.1 | — | — |
| 7.5 | 360 | 14.8 | 18.7 | 14.0 | 9.4 | 44.4 | 99.3 | 103.9 | — | — |
| 7.5 | 420 | 16.0 | 20.3 | 15.0 | 10.2 | 53.4 | 103.2 | 104.0 | — | — |

EUDRAGIT ® RS: copolymer of 65% by weight of methyl methacrylate, 30% by weight of ethyl acrylate and 5% by weight of 2-trimethylammoniumethyl methacrylate chloride.
EUDRAGIT ® FS: copolymer of 65% by weight of methyl acrylate, 25% by weight of methyl methacrylate and 10% by weight of methacrylic acid German patent application DE 10 2007 009 242.5 filed Feb. 22, 2007, and U.S. provisional application 60/908,858 filed Mar. 29, 2007, are is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A pellet ranging from 300 to 1,100 μm in diameter comprising:
a pharmaceutically active substance embedded in
a polymer matrix comprising
one or more water-insoluble polymers, and
at least one anionic polymer in an amount of 10 to 90% by weight of the polymer matrix;
with the proviso that the pellet
releases no more than 10% of said active compound in a release test according to USP in artificial gastric juice at pH 1.2 after 120 min, and
releases at least 50% of the active compound after altogether a further 300 min at pH 6.8 and/or pH 7.5;
wherein the water-insoluble polymer comprises:
a $C_1$- to $C_4$-alkyl ester of acrylic or methacrylic acid; and
a (meth)acrylate monomer having a quaternary ammonium group or a mixture of at least two (meth)acrylate monomers each having a quaternary ammonium group; and
wherein the anionic polymer comprises:
a $C_1$- to $C_4$-alkyl ester of acrylic or methacrylic acid; and
(meth)acrylate-monomers having an anionic group.

2. The pellet according to claim 1, wherein a proportion of active compound based on the pellet weight is 0.1 to 70% by weight.

3. The pellet according to claim 1, wherein a proportion of the polymer matrix based on the pellet weight is 20 to 99.9% by weight.

4. The pellet according to claim 1, which comprises at least one pharmaceutically customary excipient.

5. The pellet according to claim 1, wherein the water-insoluble polymer comprises
98 to 85% by weight of a $C_1$- to $C_4$-alkyl ester of acrylic or of methacrylic acid; and
2 to 15% by weight of a (meth)acrylate monomer having a quaternary ammonium group or a mixture of at least two (meth)acrylate monomers each having a quaternary ammonium group.

6. The pellet according to claim 1, wherein the water-insoluble polymer comprises
93 to 88% by weight of a $C_1$- to $C_4$-alkyl ester of acrylic or of methacrylic acid, and
7 to 12% by weight of a (meth)acrylate monomer having a quaternary ammonium group.

7. The pellet according to claim 1, wherein the water-insoluble polymer comprises
97 to more than 93% by weight of a $C_1$- to $C_4$-alkyl ester of acrylic or methacrylic acid; and
3 to less than 7% by weight of a (meth)acrylate monomer having a quaternary ammonium group.

8. The pellet according to claim 1, wherein the water-insoluble polymer is a mixture of at least one polymer a) and at least one polymer b);
wherein a ratio of polymer a) to polymer b) is 20:1 to 1:20;
wherein polymer a) is a water-insoluble polymer which comprises 93 to 88% by weight of a $C_1$- to $C_4$-alkyl ester of acrylic or of methacrylic acid, and
7 to 12% by weight of a (meth)acrylate monomer having a quaternary ammonium group; and
wherein polymer b) is a water-insoluble polymer which comprises 97 to more than 93% by weight of a $C_1$- to $C_4$-alkyl ester of acrylic or methacrylic acid; and
3 to less than 7% by weight of a (meth)acrylate monomer having a quaternary ammonium group.

9. The pellet according to claim 1, wherein the water-insoluble polymer is a copolymer comprising
20 to 40% by weight of ethyl acrylate, and
60 to 80% by weight of methyl methacrylate, and 0 to less than 5% by weight of acrylic acid and/or methacrylic acid.

10. The pellet according to claim 1, further comprising a water-insoluble polymer selected from the group consisting of polyvinyl acetate, a polyvinyl acetate copolymer, an ethylcellulose, a methylcellulose and mixtures thereof.

11. The pellet according to claim 1, wherein the anionic polymer comprises
25 to 95% by weight of a $C_1$- to $C_4$-alkyl ester of acrylic or of methacrylic acid; and 5 to 75% by weight of (meth)acrylate-monomers having an anionic group.

12. The pellet according to claim 1, wherein the anionic polymer is a (meth)acrylate copolymer, a polymer of i) 40 to 60% by weight of methacrylic acid and ii) 60 to 40% by weight of methyl methacrylate or 60 to 40% by weight of ethyl acrylate.

13. The pellet according to claim 1, wherein the anionic polymer is a (meth)acrylate copolymer, a polymer of 20 to 40% by weight of methacrylic acid and 80 to 60% by weight of methyl methacrylate.

14. The pellet according to claim 1, wherein the anionic polymer is a (meth)acrylate copolymer, a polymer of 10 to 30% by weight of methyl methacrylate, 50 to 70% by weight of methyl acrylate and 5 to 15% by weight of methacrylic acid.

15. The pellet according to claim 1, wherein the pharmaceutically active substance is a pharmaceutical active compound or a food supplement.

16. The pellet according to claim 1, comprising at least one pharmaceutically active substance selected from the group consisting of acamprosate, aceclofenac, acemetacin, acetylcysteine, acetylsalicylic acid, acetyltyrosine, acipimox, acitretine, alanine, alendronic acid, amethopterin, amino acids, amoxicillin, ampicillin, ascorbic acid, atorvastatin, azidocillin, aztreonam, bacampicillin, baclofen, benazepril, bendamustine, benzylpenicillin, bezafibrate, biotin, bornaprine, bumetanide, cabastine, canrenoic acid, carbamoylphenoxyacetic acid, carbidopa, carbimazole, carbocisteine, carisoprodol, cefaclor, cefadroxil, cefalexin, cefazoline, cefepime, cefetamet, cefixime, cefotaxime, cefotiam, cefoxitine, cefpodoxime, ceftazidime, ceftibutene, ceftriaxone, cefuroxime, cetirizine, chenodeoxycholic acid, chlorambucil, cidofovir, cilastatin, cilazapril, cinoxacin, ciprofloxacin, cisatracurium besilate, clavulanic acid, clodronic acid, clorazepate, cromoglicic acid, desmeninol, diclofenac, dicloxacillin, enoxacin, eprosartan, ethacrynic acid, etidronic acid, etofylline, etomidate, felbinac, felodipine, fenofibrate, fexofenadine, flavoxate, fleroxacine, flucloxacillin, flufenamic acid, flumazenil, flupirtine, flurbiprofen, fluvastatin, fosfomycin, fosinopril, furosemide, fusidic acid, gabapentin, gemfibrozil, ibandronic acid, ibuprofen, iloprost, imidapril, imipenem, indomethacin, irinotecan, isradipine, ketoprofen, lercanidipine, levodopa, levofloxacin, liothyronine, lipoic acid, lisinopril, lodoxamide, lomefloxacin, lonazolac, loracarbef, loratadine, lovastatin, mefenamic acid, meropenem, mesalazine, metamizole, methotrexate, methyldopa, mezlocillin, moexipril, montelukast, moxifloxacin, mupirocin, naproxen, natamycin, nateglinide, nedocromil, nicotinic acid, nifedipine, nilvadipine, nimodipine, nisoldipine, nitrendipine, norfloxacin, ofloxacin, olsalazine, orotic acid, oxacillin, pamidronic acid, pangamic acid, penicillamine, phenoxymethylpenicillin, pentosan polysulphate, perindopril, pethidine, pipemidic acid, piperacillin, pirenoxine, piretanide, probenecid, proglumide, propicillin, prostaglandine, quinapril, quinaprilate, ramipril, repaglinide, reserpine, risedronic acid, salicylic acid, spirapril, sulbactam, sulphasalazine, sultamicillin, tazarotene, tazobactam, telmisartan, tiagabine, tiaprofenic acid, tilidine, tiludronic acid, trandolapril, tranexamic acid, valproic acid, vigabatrine, vincamine, vinpocetine, zanamivir, zoledronic acid, zopiclone, and their salts, isomers and combinations.

17. The pellet according to claim 1, comprising a coating of a release-delaying polymer.

18. The pellet according to claim 17, comprising 1 to 10% by weight of said polymer coating, based on the pellet weight.

19. The pellet according to claim 1, which is contained in a multiparticulate pharmaceutical form, selected from the group consisting of pellet-containing tablets, minitablets, capsules, sachets, inspissated juices and combinations thereof.

20. A composition comprising pellet(s) according to claim 1.

21. A composition comprising the pellet of claim 1 and a pharmaceutically acceptable excipient.

22. A process for the production of pellets according claim 1, comprising:
   mixing the pharmaceutically active substance, the water-insoluble polymer(s) and the anionic polymer, to obtain a mixture; and
   maintaining said mixture for at least 10 sec at a temperature of at least 5° C. above the glass transition temperature of the polymer or, in the case of a polymer mixture, based on the polymer having the highest glass transition temperature;
   extruding said mixture in an extruder, to obtain an extruded mixture; and
   discharging the extruded mixture by die-face cutting with subsequent rounding to give pellets having a weight average particle size in the range from 300 to 1100 μm.

23. The process according to claim 22, further comprising:
   adding at least one pharmaceutically customary excipient to the polymer matrix in the production of the pellets.

24. The process according to claim 22, wherein the processing temperature in the extruder is 50 to 200° C.

25. A process for producing a multiparticulate pharmaceutical form which comprises the pellets according claim 1, said process comprising:
   mixing at least one pharmaceutically active substance, at least one water-insoluble polymer(s) and at least one anionic polymer, to obtain a mixture; and
   maintaining said mixture for at least 10 sec at a temperature of at least 5° C. above the glass transition temperature of the polymer or, in the case of a polymer mixture, based on the polymer having the highest glass transition temperature;
   extruding said mixture in an extruder, to obtain an extruded mixture; and
   discharging the extruded mixture by die-face cutting with subsequent rounding to give pellets having a weight average particle size in the range from 300 to 1100 μm.

26. A method of delayed release of a pharmaceutically active substance, comprising: administering a pellet according to claim 1 to an organism in need thereof 27. A composition in the form of a pellet or pellets comprising:
   a pharmaceutically active substance embedded in
   a polymer matrix comprising:
      one or more water-insoluble polymers, and
      one or more anionic polymers in an amount of 10 to 90% by weight of the polymer matrix;
      wherein the water-insoluble polymer is a neutral or essentially neutral (meth)acrylate (co)polymer which contains less than 5% anionic monomer content;
      wherein the anionic polymer is a (meth)acrylate copolymer containing 5% to 75% of anionic monomer radicals having anionic groups;
   with the proviso that the pellet
      releases no more than 10% of said active compound in a release test according to USP in artificial gastric juice at pH 1.2 after 120 min, and
      releases at least 50% of the active compound after altogether a further 300 min at pH 6.8 and/or pH 7.5.

28. The composition of claim 27, wherein said pellet or pellets have diameter(s) ranging from 300 to 1,100 μm.

29. The composition of claim 27, wherein said pellet or pellets have diameter(s) ranging from 500 to 900 μm.

30. A method of delayed release of a pharmaceutically active substance, comprising: administering a pellet according to claim 27 to an organism in need thereof.

* * * * *